United States Patent [19]

Mendoza et al.

[11] Patent Number: 4,568,497
[45] Date of Patent: Feb. 4, 1986

[54] PREPARATION OF MONOALKYLATED DIHYDROXYBENZENES

[75] Inventors: Abel Mendoza; Eric W. Otterbacher, both of Midland, Mich.

[73] Assignee: The Dow Chemical Company, Midland, Mich.

[21] Appl. No.: 614,503

[22] Filed: May 29, 1984

Related U.S. Application Data

[63] Continuation-in-part of Ser. No. 507,448, Jun. 24, 1983, abandoned.

[51] Int. Cl.$^4$ .................. C07C 121/52; C07C 69/612; C07C 41/16
[52] U.S. Cl. ............................ 260/465 F; 260/465 H; 560/61; 562/471; 562/472; 568/648; 568/649; 568/650

[58] Field of Search ............... 568/650, 803, 648, 649; 560/61; 260/465 F, 465 H; 562/471, 472

[56] References Cited

U.S. PATENT DOCUMENTS 4,328,361  5/1982  Dai .................................. 568/650 X

FOREIGN PATENT DOCUMENTS 55-127331  10/1980  Japan .
55-127332  10/1980  Japan .
55-127333  10/1980  Japan .
55-127334  10/1980  Japan .

*Primary Examiner*—Bernard Helfin

[57] ABSTRACT

Preparation of monoethers of dihydroxybenzenes from an alkenylphenol and an alkylating agent and thereafter oxidizing in the presence of an acid catalyst.

11 Claims, No Drawings

PREPARATION OF MONOALKYLATED DIHYDROXYBENZENES

REFERENCE TO COPENDING APPLICATION

This application is a continuation-in-part of Ser. No. 507,448 filed June 24, 1983 and now abandoned.

BACKGROUND OF THE INVENTION

Monoalkylated hydroquinones, resorcinols and catechols are generally difficult to prepare in high purity due to the complex separation of mono-, di- and unalkylated dihydroxybenzenes. To minimize this problem, usually low conversions are required which are an important factor in the cost of manufacture.

Monosubstituted dihydroxybenzenes are well known as polymerization inhibitors and as antioxidants. The monomethyl ether of hydroquinone is of significant economic importance. On the other hand, the use of compounds such as methyl 2-(4-hydroxyphenoxy)propionate has been described in the patent literature as a building block to prepare a wide range of biologically active materials, especially herbicides. See, for example, European Pat. No. 483 and British patent specification Nos. 1,599,121 and 1,550,574.

Japanese Patent Publications Nos. 55-127,331; 55-127,332; 55-127,333 and 55-127,334 to Ihara Chemical Industry, describe the preparation of monosubstituted hydroquinones by reacting the dimer of p-isopropenylphenol (4-methyl-2,4-bis(4-hydroxyphenyl)-pent-1-ene) with aromatic halides, ArX, where Ar is (substituted) phenyl, pryidyl or diazinyl and X is halide, to afford aromatic phenyl ethers. These materials are then thermally cracked to produce aromatic ethers of p-isopropenylphenol, which are then oxidized with $H_2O_2$ or alkyl hydroperoxide in the presence of acid to give monosubstituted hydroquinones.

U.S. Pat. No. 4,328,361 to Upjohn describes the preparation of monosubstituted hydroquinones by reacting the dimer of p-isopropenylphenol with alkyl halides, followed by reaction of these products with HCl gas to afford 4-(1-chloro-1-methylethyl)phenyl ethers. These materials give monosubstituted hydroquinones when reacted with $H_2O_2$ or alkyl hydroperoxide.

It is known that p-isopropenylphenol (p-IPP) can be alkylated under a variety of conditions with certain alkylating agents. For example, the alkylation of p-IPP with excess allyl chloride has been taught in Azerbaidzbanskii Khimicheskii Zhurnal, No. 6, pp. 52–57 (1979). Another example is the reaction of o-IPP with excess epichlorohydrin in Italian Pat. No. 705,414. Further examples involve the alkylation of p-IPP with various aromatic halides as in Japanese Kokai Tokkyo Koho No. 56-166138.

It is also known that isopropenylbenzenes containing no substituents whose reactivity could complicate the reaction can be oxidized to phenols using hydrogen peroxide and a strong acid catalyst. See German No. 2,214,971 to Upjohn.

However, the known art does not disclose or suggest alkylations of alkenylphenols such as isopropenylphenols and subsequent oxidations of the alkenylphenyl ethers where the alkylating agent is not an aromatic halide. When the alkylating agent is an aliphatic halide, sometimes it can be sensitive to hydrolysis and dehydrochlorination in competition with alkylation. Similarly, the ether moiety in aliphatic isopropenylphenyl ethers can be sensitive to oxidation or hydrolysis in competition with oxidation of the isopropenyl moiety. By comparison, all of these complications are not present in aromatic ethers of isopropenylphenol.

SUMMARY OF THE INVENTION

The present invention provides for the efficient and selective preparation of monoethers of dihydroxybenzenes by reacting alkenylphenols having the formula

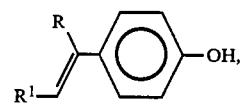

wherein R and $R^1$ are independently H or lower alkyl or where R and $R^1$ together comprise $-(CH_2-)_x$ where X is 3, 4, 5 or 6 with alkylating agents in the presence of bases to afford the phenyl ethers. These in turn are oxidized with $H_2O_2$ to give the monosubstituted benzene diols. If desired, optically active materials may be made by this process.

The invention also provides certain novel compounds prepared by the process of this invention.

DETAILED DESCRIPTION OF THE INVENTION

The process of the present invention may be schematically represented as follows:

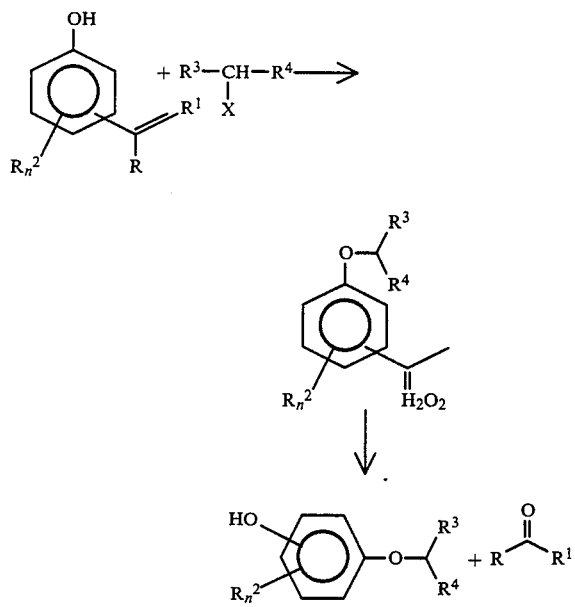

In the above reactions, $R^2$ represents halo, alkoxy, CN, or lower alkyl; n represents 0, 1, 2, 3 or 4; $R^3$ represents H, lower alkyl, alkoxy, carboxy, or —CN and $R^4$ represents H, lower alkyl, alkoxy, carboxy, or —CN. In the case of carboxy substitution, the ester can be substituted by H, lower alkyl or a glycol ether. When employing difunctional or trifunctional alkylating agents the corresponding di- or trialkenylphenol ethers are obtained.

In the alkylation (first step of the reaction), it is generally desirable to employ one equivalent of phenol and one equivalent of alkylating agent and a temperature of 0°–200° C., although higher temperatures may be employed if at superatmospheric pressures. The preferred temperatures are 25°–125° C. It is known that the alkylation of phenols with alcohols may be carried out in the absence of a base. However, for most alkylating agents, a base is advantageously employed, preferably in an amount of about 1 equivalent of base per equivalent of phenol. The time of reaction depends on temperature and solvent and is generally 0.1–10 hours. Atmospheric pressure is preferred. Solvents such as alcohols, ketones and polar aprotic solvents such as, for example, sulfoxides, N,N'-disubstituted amides and nitriles may be employed and bases such as alkali metal carbonates, alkali metal hydroxides and alkali metal hydrides may be used.

Alkylating agents that are useful in the process of this invention include, for example, α-haloacids and esters such as methyl 2-chloropropionate and methyl chloroacetate, and the corresponding acids, dimethylsulfate, chloroacetonitrile, allyl bromide and ethylene carbonate.

The alkylation may be carried out in single phase or two phase systems using appropriate conditions as known in the art.

In the oxidation (second step of the reaction), it is generally desirable to employ one equivalent of alkenylphenyl ether, one equivalent of hydrogen peroxide or alkyl hydroperoxide per alkenyl radical and a catalytic amount of a strong acid (e.g. $H_2SO_4$, phosphoric, sulfonic acids, hydrochloric acid, and including strong acid ion exchange resins), preferably in a reaction medium at a temperature between 25° C. and 100° C. The reaction medium may be, for example, water, a carboxylic acid, an alcohol, a ketone, an ester, a halogenated alkane, a halogenated aromatic, or an ether. The reaction time is advantageously 0.001–5.0 hours, depending on conditions like temperature and the reaction medium. The oxidation is preferably carried out in a single phase system although two phase systems may be used if desired.

When carrying out the oxidation reaction in an alcohol carboxylic acids are converted to the corresponding ester simultaneously with the oxidation of the alkenylphenol portion of the molecule.

A continuous process wherein heat is removed as it is generated by the reaction is preferred. When hydrolyzable groups are present, it is desirable that the reaction be terminated before significant hydrolysis occurs.

The invention is further illustrated by the following examples wherein all parts are by weight unless otherwise specified.

EXAMPLE 1

Preparation of methyl 2-(4-(1-methylethenyl)phenoxy)propanoate

A 247 g-portion of p-isopropenylphenol was dissolved in 1.3 liters dimethylsulfoxide (DMSO). This solution was degassed three times by reducing the pressure until the DMSO boiled vigorously, then releasing to atmospheric pressure with nitrogen. Under nitrogen, an equimolar amount of aqueous 50% NaOH solution was added. The reaction mixture was heated under reduced pressure to remove water and DMSO overhead at up to 123° C. head temperature at 100 mmHg pressure. The reaction mixture was cooled to about 80° C. and methyl 2-chloropropanoate (237 g = 1.05 equivalents) was added over 7 times. Cooling was used to keep the temperature at 79°–86° C. The temperature was kept at 72°–80° C. for 5 minutes. The reaction mixture was then cooled to 20° C. within 10 minutes. The reaction mixture was poured into 1 liter $CH_2Cl_2$ and 1 liter 5% aqueous NaOH. The aqueous layer was extracted once with 100 ml $CH_2Cl_2$. The combined organic layers were washed with two 150 ml portions of 5% aqueous NaOH and dried with $Na_2SO_4$. Removal of solvent gave 348 g of a brown liquid. Analysis by gas chromatography using an internal standard established purity at 98% of methyl 2-(4-(1-methylethenyl)phenoxy)propanoate, corresponding to an 84% yield.

EXAMPLE 2

Preparation of methyl 2-(4-hydroxyphenoxy)propanoate

A. An 86.0 g-portion of methyl 2-(4-(1-methylethenyl)phenoxy)propanoate was dissolved in 360 ml glacial acetic acid. An equimolar portion of 30% aqueous $H_2O_2$ was added. The solution was cooled to 10° C. and 7.6 mol % of 98% $H_2SO_4$ was added. The solution was allowed to slowly warm to 35° C. over 11 minutes at which point the ice bath was put back on. The temperature peaked at 84° C. two minutes later. The reaction mixture was allowed to cool slowly to 36° C. over 25 minutes. A 26 g-portion of 20% aqueous $Na_2SO_3$ was added, followed by 900 ml water. The mixture was extracted with four 200 ml-portions of $CH_2Cl_2$. The combined organic layers were washed with two 200 ml-portions and one 400 ml-portion of 5% aqueous $NaHCO_3$. The organic layer was dried with $Na_2SO_4$. Removal of solvent gave 74.8 of 94% pure methyl 2-(4-hydroxyphenoxy)propanoate, corresponding to a 92% yield. Distillation under reduced pressure gave 59.3 g of methyl 2-(4-hydroxyphenoxy)propanoate (b.p. 154°–155° C./4 torr) corresponding to a 77% yield.

B. A solution of 10 g methyl 2-(4-(1-methylethenyl)phenoxy)propanoate, 1.2 equivalents 30% aqueous $H_2O_2$ in 30 ml acetone, and 0.1 equivalent 98% $H_2SO_4$ was refluxed for about 2 hours. Workup gave a 57% yield of methyl 2-(4-hydroxyphenoxy)propanoate.

C. Hydrogen peroxide (67% $H_2O_2$, 0.60 equivalents) was added to a mixture of 0.005 equivalents of Dowex ® MSC-1 sulfonic acid resin in the proton form, 0.050 equivalents 2-(4-(1-methylethenyl)phenoxy)propanoic acid (prepared by base hydrolysis of methyl 2-(4-(1-methylethenyl)phenoxy)propanoate), and 11 ml methanol at room temperature. The mixture was refluxed about 10 hours. (The oxidation was complete after about 1.5 hour, but about 10 hours were required for the simultaneous esterification.) Workup gave 8.3 g of methyl 2-(4-hydroxyphenoxy)propanoate containing a small amount of 2-(4-hydroxyphenoxy)propanoic acid.

EXAMPLE 3

Preparation of methyl 2-(4-(1-methylethenyl)-phenoxy)acetate

A 6.7 g-portion of p-isopropenyl phenol and 5.4 g of methyl chloroacetate in 40 ml of dimethylformamide was heated at 110° C. for 2.5 hours in the presence of 6.9 g of $K_2CO_3$. The mixture was cooled, and the insoluble solids filtered. Removal of the solvent, followed by vacuum distillation afforded 7.6 g of a white solid with a b.p. of 110°–112° C., 0.3 torr, and a m.p. of 64°–66° C., identified by spectroscopic means as methyl 2-(4-(1-methylethenyl)phenoxy)acetate.

EXAMPLE 4

Preparation of methyl 2-(4-(1-cyclohexene)phenoxy)acetate

A 17.4 g portion of 1-(4-hydroxyphenyl)cyclohexene and 12.9 g of methyl chloroacetate in 80 ml of acetonitrile was heated at 80° C. for 4.5 hours in the presence of 27.6 g of $K_2CO_3$. The mixture was cooled and the insoluble solids filtered. Removal of the solvent, followed by washing of the product with hexane, afforded 20.3 g of a white solid identified by spectroscopic means as 2-(4-(1-cyclohexene)phenoxy)acetate.

EXAMPLE 5

Preparation of methyl 2-(4-hydroxyphenoxy)acetate

A. To a 6.2 g-portion of 2-(4-(1-methylethenyl)-phenoxy)acetate and 3.0 ml of 30% $H_2O_2$ dissolved in 30 ml of glacial acetic acid was added 0.1 g of concentrated sulfuric acid at 10° C. The solution was allowed to warm up to 25° C. An exothermic reaction took place, and the temperature increased to 55° C. in a few minutes. The solution was cooled to 25° C. and added to 50 ml of water. The aqueous solution was extracted with two 50 ml-portions of $CH_2Cl_2$ and dried with $MgSO_4$. Removal of the solvent under vacuum afforded 4.3 g of a solid identified by spectroscopic means as methyl 2-(4-hydroxyphenoxy)acetate.

B. Using similar conditions, a 7.4 g portion of methyl 2-(4-(1-cyclohexene)phenoxy)acetate was converted to methyl 2-(4-hydroxyphenoxy)acetate. This was accomplished with 6.0 ml of 30% $H_2O_2$, at 30°-60° C. over a period of one hour, in the presence of 0.1 g of concentrated sulfuric acid. A similar workup afforded 4.5 g of an oil containing 60% of a product identified by a spectroscopic means as methyl 2-(4-hydroxyphenoxy)acetate.

EXAMPLE 6

Preparation of 2-ethoxyethyl 2-(4(1-methylethenyl)phenoxy)propanoate

Using essentially the same conditions as given above for the preparation of methyl 2-(4-(1-methylethenyl)-phenoxy)propanoate, a 41.0 g portion of p-isopropenylphenol was converted to 2-ethoxyethyl 2-(4-(1-methylethenyl)phenoxy)propanoate in 79% yield.

EXAMPLE 7

Preparation of 2-ethoxyethyl 2-(4-hydroxyphenoxy)propanoate

Using essentially the same conditions as given above for the preparation of 2-methyl 2-(4-hydroxyphenoxy)-propanoate, 54.3 g of 2-ethoxy ethyl 2-(4-(1-methylethenyl)phenoxy)propanoate was converted to 2-ethoxyethyl 2-(4-hydroxyphenoxy)propanoate in 78% yield.

EXAMPLE 8

Preparation of 1-Methoxy-4-(1-methylethenyl)benzene

A 50 g-portion of p-isopropenylphenol was dissolved in 250 ml methanol and 48.5 g of aqueous 40% NaOH was added. Then 42.5 ml dimethylsulfate was added causing the reaction mixture to reflux at about 45° C. The reaction mixture was stirred about 20 minutes, then diluted with 250 ml of aqueous 2% NaOH. Methanol was removed under reduced pressure. A 250 ml portion of ether was added. The ethereal layer was washed with two 100 ml-portions of aqueous 5% NaOH, two 100 ml-portions of water, and dried over $Na_2SO_4$. Removal of solvent gave 43.1 g of an oil which solidified on standing. Distillation gave 37.3 g of 1-methoxy-4-(1-methylethenyl)benzene as a white solid, bp 64°-65° C./5 torr.

EXAMPLE 9

Preparation of 4-Methoxyphenol

A mixture of 0.50 g of 1-methoxy-4-(1-methylethenyl)benzene, an equimolar portion of aqueous 30% $H_2O_2$, 10 ml methanol, and 0.09 g 98% $H_2SO_4$ were prepared. After about 2 hours at reflux, the reaction mixture was poured into 50 ml water followed by extraction with three 10-15 ml-portions of ether. The combined organic layers were dried over $Na_2SO_4$. Removal of solvent gave 0.65 g of orange-brown liquid shown to contain about 52% of 4-methoxyphenol, corresponding to about 80% yield of 4-methoxyphenol.

EXAMPLE 10

Preparation of 2-(4-(1-Methylethenyl)phenoxy)ethanol

A mixture of 20 g p-isopropenylphenol, 1.1 equivalents ethylene carbonate, 0.02 equivalent potassium fluoride dihydrate, and 200 ml N,N-dimethylformamide (DMF) was heated at about 150° C. for about 1.5 hours. After removal of DMF under reduced pressure, the crude product was distilled. 2-(4-(1-Methylethenyl)-phenoxy)ethanol, bp 143° C./7 torr, was obtained as a white solid in 69% yield.

EXAMPLE 11

Preparation of 4-(2-Hydroxyethoxy)phenol

To a mixture of 2.50 g 2-(4-(1-methylethenyl)phenoxy)ethanol, 10 ml methanol, and 1.1 equivalents 50% aqueous $H_2O_2$ were added 0.1 equivalent 98% $H_2SO_4$. The reaction mixture warmed itself to reflux which subsided in a few minutes. After addition of 0.2 equivalent $Na_2SO_3$, methanol was removed under reduced pressure. The residue was taken up in ether, dried over $Na_2SO_4$ and $NaHCO_3$, and filtered. Removal of solvent left 4-(2-(hydroxyethoxy)phenol in quantitative yield.

EXAMPLE 12

Preparation of 1-(Methylethenyl)-4-(2-propenyloxy)benzene

A 10 g-portion of p-isopropenylphenol, 1.0 equivalent allyl bromide, 1.0 equivalent $K_2CO_3$, and 20 ml acetone were mixed and refluxed overnight. The reaction mixture was poured into 60 ml water and extracted with two portions of ether. The combined ether layers were washed with two portions of 10% aqueous NaOH, two portions of saturated aqueous NaCl and dried over $K_2CO_3$. Removal of solvent followed by distillation under reduced pressure gave a 63% yield of 1-(1-methylethenyl)-4-(2-propenyloxy)benzene, mp 22°-23° C.

EXAMPLE 13

Preparation of 4-Allyloxyphenol

A 2.3 g-portion of 1-(1-methylethenyl)-4-(2-propenyloxy)benzene was converted to 4-allyloxyphenol in 79% yield using conditions similar to those used for the preparation of 4-(2-hydroxyethoxy)phenol (Example 10).

EXAMPLE 14

Preparation of 2-(4-(1-Methylethenyl)phenoxy)acetonitrile

A 6.7 g-portion of p-isopropenyl phenol and 4.6 g of chloroacetonitrile in 40 ml of acetonitrile were heated at 80° C. for 3.5 hours in the presence of 13.8 g of $K_2CO_3$. The mixture was cooled, and the insoluble solids filtered. Removal of the solvent, followed by vacuum distillation afforded 6.8 g of a clear liquid, bp 89°–91° C., 0.1 torr, identified by spectroscopic means as 2-(4-(1-methylethenyl)phenoxy)acetonitrile.

EXAMPLE 15

Preparation of 2-(4-Hydroxyphenoxy)acetonitrile

Using essentially the same conditions previously described for the preparation of methyl 2-(4-hydroxyphenoxy)acetate (Example 5), a 5.3 g-portion of 2-(4(1-methylethenyl)phenoxy)acetonitrile was converted to 2-(4-hydroxyphenoxy)acetonitrile in 73% yield, bp 133°–134° C., 0.1 torr.

EXAMPLE 16

Preparation of optically active methyl 2-(4-(1-methylethenyl)phenoxy)propanoate

An anhydrous solution of the sodium salt of p-isopropenylphenol in DMSO (prepared from 5.00 g p-isopropenylphenol, 2.98 g 50% NaOH, and 60 ml DMSO as in Example 1) was added over about 15 minutes to a solution of 45.73 g L(−) methyl 2-chloropropanoate in 50 ml DMSO. The temperature was kept at about 25° C. using an ice bath. The reaction mixture was stirred at about 25° C. for about 45 minutes more. Workup and distillation gave optically active methyl 2-(4-(1-methylethenyl)phenoxy)propanoate containing about 90% of the R enantiomer as determined by nuclear magnetic resonance spectrometry in the presence of an optically active shift reagent.

EXAMPLE 17

Preparation of optically active methyl 2-(4-hydroxyphenoxy)propanoate

Optically active methyl 2-(4-(1-methylethenyl)-phenoxy)propanoate prepared by alkylation of p-isopropenylphenol with L(−) methyl 2-chloropropanoate was oxidized as in Example 2A. The resulting optically active methyl 2-(4-hydroxyphenoxy)propanoate was found to contain about 90% of the R enantiomer as determined by nuclear magnetic resonance spectrometery in the presence of an optically active shift reagent.

Various modifications may be made in the present invention without departing from the spirit or scope thereof and it is understood that we limit ourselves only as defined in the appended claims.

We claim:

1. A process for preparing monoethers of dihydroxybenzenes which comprises reacting an alkenylphenol having the formula

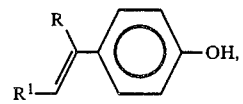

wherein R and $R^1$ are independently H or lower alkyl or where R and $R^1$ together comprise $-(CH_2)-_x$ where X is 3, 4, 5, or 6, in the presence of a polar solvent with a substituted aliphatic alkylating agent containing up to about 10 carbon atoms and at a temperature of from 0° To 200° C. and thereafter oxidizing with hydrogen peroxide or an alkyl hydroperoxide in the presence of a strong acid catalyst at a temperature of from 25° to 100° C.

2. Process of claim 1 wherein the alkenylphenol is isopropenylphenol.

3. Process of claim 2 wherein the alkylating agent is a 2-chloropropionic acid or ester, a chloroacetic acid or ester of chloroacetonitrile.

4. Process of claim 3 wherein the ester is the methyl ester or the 2-ethoxyethyl ester.

5. Process of claim 3 wherein the solvent for the alkylation reaction is dimethylformamide, acetonitrile, dimethylsulfoxide, acetone or methanol.

6. Process of claim 1 wherein the alkylation reaction is carried out in the presence of a base.

7. Process of claim 6 wherein the base is potassium carbonate, sodium carbonate, sodium hydroxide or potassium hydroxide.

8. Process of claim 1 wherein the oxidation reaction is carried out in a reaction medium.

9. Process of claim 8 wherein the reaction medium for the oxidation reaction is acetic acid, methanol or acetone.

10. Process of claim 9 wherein the acid catalyst is sulfuric or phosphoric acid.

11. Process of claim 8 wherein the oxidation is caused by hydrogen peroxide.

* * * * *

UNITED STATES PATENT AND TRADEMARK OFFICE
CERTIFICATE OF CORRECTION

PATENT NO. : 4,568,497

DATED : February 4, 1986

INVENTOR(S) : Abel Mendoza & Eric W. Otterbacher

It is certified that error appears in the above-identified patent and that said Letters Patent is hereby corrected as shown below:

Column 1, line 32, "phenyl, pryidyl or diazinyl" should read -- phenyl, pyridyl or diazinyl --.

Column 3, line 35, "advantageously 0.001-5.0 hours" should read -- advantageously 0.01-5.0 hours --.

Column 3, line 66, "over 7 times." should read -- over 7 minutes. --.

Column 5, line 41, "2-(4(1-methylethenyl)phenoxy)propanoate" should read -- 2-(4-(1-methylethenyl)phenoxy)propanoate --.

Column 6, line 44, "4-(2-(hydroxyethoxy)phenol" should read -- 4-(2-hydroxyethoxy)phenol --.

Column 6, line 48, "1-(Methylethenyl)-4-(2-propenyloxy)-benzene should read -- 1-(1-Methylethenyl)-4-(2-propenyloxy)-benzene --.

UNITED STATES PATENT AND TRADEMARK OFFICE
CERTIFICATE OF CORRECTION

PATENT NO. : 4,568,497

DATED : February 4, 1986

INVENTOR(S) : Abel Mendoza & Eric W. Otterbacher

It is certified that error appears in the above-identified patent and that said Letters Patent is hereby corrected as shown below:

Column 7, line 19, "a 5.3 g-portion of 2-(4(1-" should read -- a 5.3 g-portion of 2-(4-(1- --.

Column 8, lines 1 & 2, "resonance spectrometery in the" should read -- resonance spectrometry in the --.

Signed and Sealed this

Eleventh Day of November, 1986

*Attest:*

DONALD J. QUIGG

*Attesting Officer*     *Commissioner of Patents and Trademarks*